United States Patent
Pescatore

(10) Patent No.: US 7,507,027 B2
(45) Date of Patent: Mar. 24, 2009

(54) METHOD AND APPARATUS FOR POSITIONING AN OBJECT WITH RESPECT TO THE ISOCENTER OF AN ACQUISITION SYSTEM

(75) Inventor: Jeremie Pescatore, Paris (FR)

(73) Assignee: General Electric Company, Schenectady, NY (US)

( * ) Notice: Subject to any disclaimer, the term of this patent is extended or adjusted under 35 U.S.C. 154(b) by 12 days.

(21) Appl. No.: 12/020,359

(22) Filed: Jan. 25, 2008

(65) Prior Publication Data
US 2008/0118037 A1    May 22, 2008

Related U.S. Application Data

(62) Division of application No. 10/891,664, filed on Jul. 15, 2004, now Pat. No. 7,357,573.

(30) Foreign Application Priority Data
Nov. 28, 2003    (FR) .................................. 03 50926

(51) Int. Cl.
*A61B 6/08* (2006.01)
(52) U.S. Cl. ...................... 378/205; 378/163
(58) Field of Classification Search .............. 378/20, 378/41, 42, 163, 164, 205–207; 600/426, 600/427, 429
See application file for complete search history.

(56) References Cited
U.S. PATENT DOCUMENTS 4,296,329 A * 10/1981 Mirabella ................ 250/491.1
4,578,806 A * 3/1986 Grass et al. ................ 378/162
5,117,829 A * 6/1992 Miller et al. ................ 600/427
5,129,911 A    7/1992 Siczek et al.
5,291,540 A    3/1994 Futamata (Continued)

FOREIGN PATENT DOCUMENTS
EP    0763343    3/1997

(Continued)

OTHER PUBLICATIONS

Grutzner et al., "Clinical Study for Registration-Free 3D-Navigation with the SIREMOBIL Iso-C3D Mobile C-Arm", electromedica 71 (2003) No. 1 (Supp.), pp. 7-16.

*Primary Examiner*—Edward J Glick
*Assistant Examiner*—Thomas R Artman
(74) *Attorney, Agent, or Firm*—McAndrews, Held & Malloy, Ltd.; Peter J. Vogel; Michael A. Dellapenna

(57) ABSTRACT

Certain embodiments of the present invention relate to a system and method for object and isocenter alignment in an imaging system. The system includes an electromagnetic, an electromagnetic receiver, and an imaging unit for determining an isocenter of an imaging scanner based on information from the electromagnetic receiver. The imaging unit identifies the isocenter based on a plurality of electromagnetic position measurements. The imaging unit identifies a center of an object to be imaged based on information from a second electromagnetic receiver. The imaging unit repositions the object based on the isocenter. In an embodiment, the emitter is located on the object, the first receiver is located on a detector, and the second receiver is located on a tool for identifying a center of the object or a portion of the object.

20 Claims, 7 Drawing Sheets

U.S. PATENT DOCUMENTS

| | | | |
|---|---|---|---|
| 6,120,180 A * | 9/2000 | Graumann | 378/206 |
| 6,260,999 B1 | 7/2001 | Wofford et al. | |
| 6,309,103 B1 * | 10/2001 | Sano | 378/205 |
| 6,490,473 B1 | 12/2002 | Katznelson et al. | |
| 6,535,574 B1 * | 3/2003 | Collins et al. | 378/65 |
| 6,738,656 B1 | 5/2004 | Ferre et al. | |
| 6,845,260 B2 | 1/2005 | Liu et al. | |
| 2002/0193685 A1 | 12/2002 | Mate et al. | |
| 2004/0158146 A1 | 8/2004 | Mate et al. | |

FOREIGN PATENT DOCUMENTS

| | | |
|---|---|---|
| EP | 1114617 | 7/2001 |
| GB | 2356117 | 5/2001 |
| WO | WO 9953333 | 10/1999 |

* cited by examiner

METHOD AND APPARATUS FOR POSITIONING AN OBJECT WITH RESPECT TO THE ISOCENTER OF AN ACQUISITION SYSTEM

RELATED APPLICATIONS

The present application relates to, and claims priority as a divisional from, U.S. patent application Ser. No. 10/891,664, filed on Jul. 15, 2004, entitled "Method and Apparatus for Positioning an Object with Respect to the Isocenter of an Acquisition System," which in turn claims priority to French Patent Application No. 0350926, filed on Nov. 28, 2003, and entitled "Semi-Automatic positioning of an organ for 3D reconstruction using EM navigation devices", each of which is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to object positioning for image acquisition. In particular, the present invention relates to object positioning with respect to the isocenter of an acquisition system for image acquisition.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

Obtaining an imaging an object or patient using an imaging system typically involves exposing the object or patient to a certain amount of radiation, such as x-ray radiation. The more exposures or image scans executed, the greater the radiation exposure of the object or patient. Increased radiation exposure raises health concerns for a patient being imaged. Additionally, health and safety standards limit radiation dosage for a patient imaging scan. Health and safety standards may impact image quality due to reduced or lower quality image scans. Thus, a system that minimizes radiation dosage and exposure to a patient would be highly desirable.

Tomographic reconstruction reconstructs tomographic images for two-dimensional and three-dimensional image scans. Tomographic reconstruction reconstructs an image from image data projections (such as x-ray projections) generated in an image acquisition system. Data from multiple projections are combined to produce an image describing the object. Often, two-dimensional slices are reconstructed from scans of a three-dimensional object. The two-dimensional slices may be combined to construct a three-dimensional image.

During tomographic reconstruction, an object or patient organ being imaged is placed at or near a center of rotation (i.e., the isocenter) of an acquisition system being used (an x-ray source and detector, for example). For reconstruction of two-dimensional x-ray views acquired on a C-arm imaging system, for example, centering of an object or organ is usually performed under continuous two-dimensional x-ray fluoroscopy. That is, several lateral and frontal projections are taken until an optimal position has been found from the specific x-ray acquisitions. Therefore, a method of positioning an object or patient organ at or near the isocenter of an image acquisition system would be highly desirable.

Therefore, a need exists for an improved object positioning system for positioning an object at the isocenter of an acquisition system for image acquisition.

BRIEF SUMMARY OF THE INVENTION

Certain embodiments of the present invention provide a method and system for isocenter determination and alignment in a tomographic image reconstruction system. In a certain embodiment, the method includes acquiring two x-ray projections in an imaging system, determining an isocenter for the imaging system, locating a center position of an object to be imaged, and positioning the center position of the object with respect to the isocenter. The isocenter may be determined based on a segment intersecting the x-ray projections. Electromagnetic navigation devices, such as electromagnetic emitters and receivers, may be used to determine the isocenter and locate the center position. The object may be manually and/or automatically moved to position the center position with respect to the isocenter.

In an embodiment, the method includes acquiring at least three position measurements for an electromagnetic receiver attached to a detector in an imaging system and computing an isocenter with respect to an electromagnetic emitter based on the position measurements. The method may also include indicating a center position of an object and moving the object such that the isocenter and the center position are aligned. The object may be manually and/or automatically moved such that the isocenter and the center position match. The isocenter may be computed based on a center of the position measurements.

In an embodiment, the method includes calculating an approximate focal distance in an imaging system, determining position and orientation information for an electromagnetic receiver with respect to an electromagnetic emitter in the imaging system, and identifying an isocenter for the imaging system using the position and orientation information and approximate focal distance. The method may also include back-projecting the position information to identify the isocenter. Additionally, the method may include indicating a center position of an object around which a tomographic acquisition may be performed and moving the object such that the isocenter and the center position are aligned. The center position may be indicated using a second electromagnetic receiver. The object may be automatically and/or manually moved such that the isocenter and the center position are aligned.

In a certain embodiment, the system includes an electromagnetic emitter for generating a magnetic field, an electromagnetic receiver for detecting the magnetic field from the electromagnetic emitter, and an imaging unit for determining an isocenter of an imaging scanner based on information from the electromagnetic receiver. The electromagnetic receiver may be located on a detector for acquiring image data. The electromagnetic emitter may be located on an object to be imaged. Alternatively, the receiver may be located on the object, and the emitter may be located on the detector. The imaging unit may identify the isocenter based on a plurality of position measurements from the electromagnetic receiver. The imaging unit may also identify the isocenter based on a plurality of x-ray projections and a plurality of position measurements from the electromagnetic receiver. The imaging unit may reposition an object to be imaged based on the isocenter.

The system may also include a second electromagnetic receiver for detecting the magnetic field from the electromagnetic emitter. The second electromagnetic receiver may be located on a tool for identifying a center of an object to be imaged. The imaging unit may identify a center of an object based on information from the second electromagnetic receiver.

Figure 1:
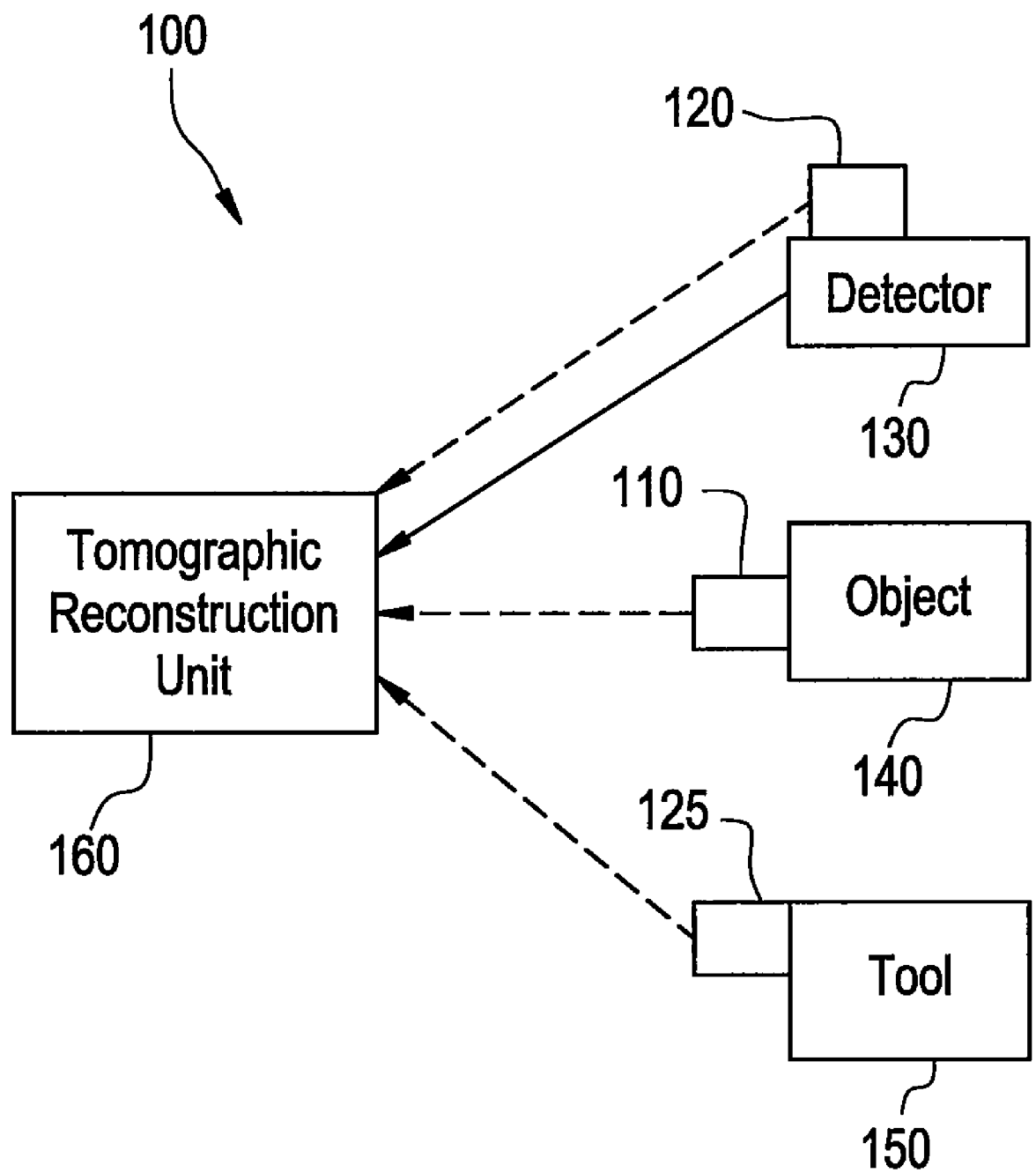
FIG. 1 illustrates a magnetic resonance imaging system used in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

For illustration purposes only, certain embodiments of the present invention are described in relation to an x-ray imaging system. Embodiments of the present invention may apply to a plurality of modalities, such as magnetic resonance (MR) imaging, x-ray imaging, computed tomographic (CT) imaging, electron beam tomographic (EBT) imaging, positron emission tomographic (PET) imaging, single photon emission computed tomographic (SPECT) imaging, and ultrasound imaging.

FIG. 1 illustrates an object positioning system 100 for x-ray imaging used in accordance with an embodiment of the present invention. The system 100 includes an electromagnetic (EM) emitter 110, EM receivers 120, 125, an x-ray detector 130, an x-ray source 135, an object 140, a tool 150, and a tomographic reconstruction unit 160. The EM emitter 110 is attached to the object 140. The EM receiver 120 is attached to the x-ray detector 130. The EM receiver 125 is attached to the tool 150.

The EM emitter 110 and EM receivers 120, 125 are electromagnetic navigation devices. For example, the EM emitter 110 and EM receivers 120, 125 may include wire coil trios used to locate a subject based on electromagnetic fields generated. The EM navigation devices use a variety of methods to locate a subject based on information, such as field strength and phase. In an embodiment, EM navigation devices may be configured according to an industry standard coil architecture (ISCA).

The EM emitter 110 is located on or in, for example, the object 140, such as a patient, organ, or other object to be reconstructed. The EM emitter 110 broadcasts a magnetic field. Characteristics of the magnetic field produced by the emitter 110 may be used to identify the position of the emitter 110 and, thus, the object 140, with respect to the receivers 120 and/or 125 in a coordinate system.

The EM receiver 120 is located on or in, for example, the x-ray detector 130. The x-ray detector 130 detects rays generated from the x-ray source 135. The EM receiver 120 detects a magnetic field from the EM emitter 110 on the object 140. The EM receiver 120 transmits data regarding the field from the EM emitter 110 to the tomographic reconstruction unit 160.

The EM receiver 125 is located on or in, for example, the tool 150. The tool 150 is a pin, clamp, rod, or other implement, for example, that may be used to point to a center of the object 140 being reconstructed. The EM receiver 125 detects a magnetic field from the EM emitter 110. The EM receiver 125 transmits data regarding the field from the emitter 110 to the reconstruction unit 160.

In an alternative embodiment, the EM receiver 120, 125 is located on the object 140. The EM emitter 110 is located on the tool 150 or the detector 130.

The tomographic reconstruction unit 160 (or other imaging unit) receives data from the EM receivers 120, 125 to determine the location of the object 140 and the tool 150 and to determine the isocenter of the system 100. The tomographic reconstruction unit 160 aligns the center of the object 140 with the isocenter of the system 100 to optimize operations, such as three-dimensional image reconstruction. The tomographic reconstruction unit 160 may be implemented in hardware and/or in software. The reconstruction unit 160 may be a dedicated processor or part of a general purpose computer. The reconstruction unit 160 may be embodied in a separate unit or may be combined with other components of an imaging system.

In operation, a working reconstruction position may be determined using two EM receiver 120 positions with or without x-ray acquisition (frontal and lateral, for example). The source 135 generates x-ray projections at frontal and lateral positions, for example, through the object 140. The receiver 120 and detector 130 identify the frontal and lateral projections. In an embodiment, information regarding the projections may be obtained during current and/or prior calibration. The frontal and lateral projection vectors generally do not intersect each other. An isocenter for the system 100 may be determined at the midpoint of a segment orthogonally connecting the projections. Since the EM receiver 120 is attached to the detector 130 and the EM emitter 110 is attached to the object 140, the isocenter is determined with respect to the object 140 (the emitter 110).

In an alternative embodiment, a focal distance for the x-ray projections may be approximately determined. Using the approximate focal distance and EM positioning information, projection vectors and focal points may be determined without acquiring x-ray images. Once the vectors and focal points are determined, the isocenter may be identified from the midpoint of the connecting segment, as described above.

After the isocenter has been determined in relation to the emitter 110 position, the tool 150 with EM receiver 125 is used to identify a center position of the object 140 or portion of the object 140 around which tomographic acquisition is to be performed. For example, a physician places a clamp with an EM receiver at the center of an organ to be reconstructed in the system 100. The EM emitter 110 and the EM receiver 125 may be used to determine the position of the tool 150.

Then, a repositioning system (not shown) is used to reposition the object 140 such that the center of the object 140 identified above is aligned with respect to the isocenter of the system 100. The repositioning system may be a manual system and/or an automated system. For example, the repositioning system may be a manual table or support moved by a technician until the object 140 center and isocenter are approximately aligned. Alternatively, for example, a motorized table or support may automatically reposition the object 140 based on isocenter and center data.

In an alternative embodiment, the isocenter may be determined without radiation (e.g., x-ray) exposures. The detector 130 is positioned as during a tomographic image acquisition, but x-rays are not produced from the source 135. The EM receiver 120 at the center of the detector 130 determines three or more positions of the center of the detector 130 in relation to the emitter 110. The tomographic reconstruction unit 160 receives the position data. If three positions are acquired, the three positions form a triangle. The isocenter may be determined at the center of the triangle. If more than three positions are acquired, the positions form a circle. The isocenter may be identified at the center of the mean circle projected in the mean plane of the acquired detector 130 positions.

Alternatively, the reconstruction unit 160 may determine an EM orientation of the acquired detector 130 positions using the emitter 110 and receiver 120. An approximate source-to-image distance may be determined through calibration or other information. The detector 130 positions may then be back-projected. The isocenter is the midpoint of a segment connecting the projections, as described above.

As described above, after the isocenter has been determined, the tool 150 identifies the desired center of tomographic reconstruction for the object 140. The object 140 is manually and/or automatically repositioned such that the center is positioned with respect to the isocenter of the imaging system.

Figure 2:
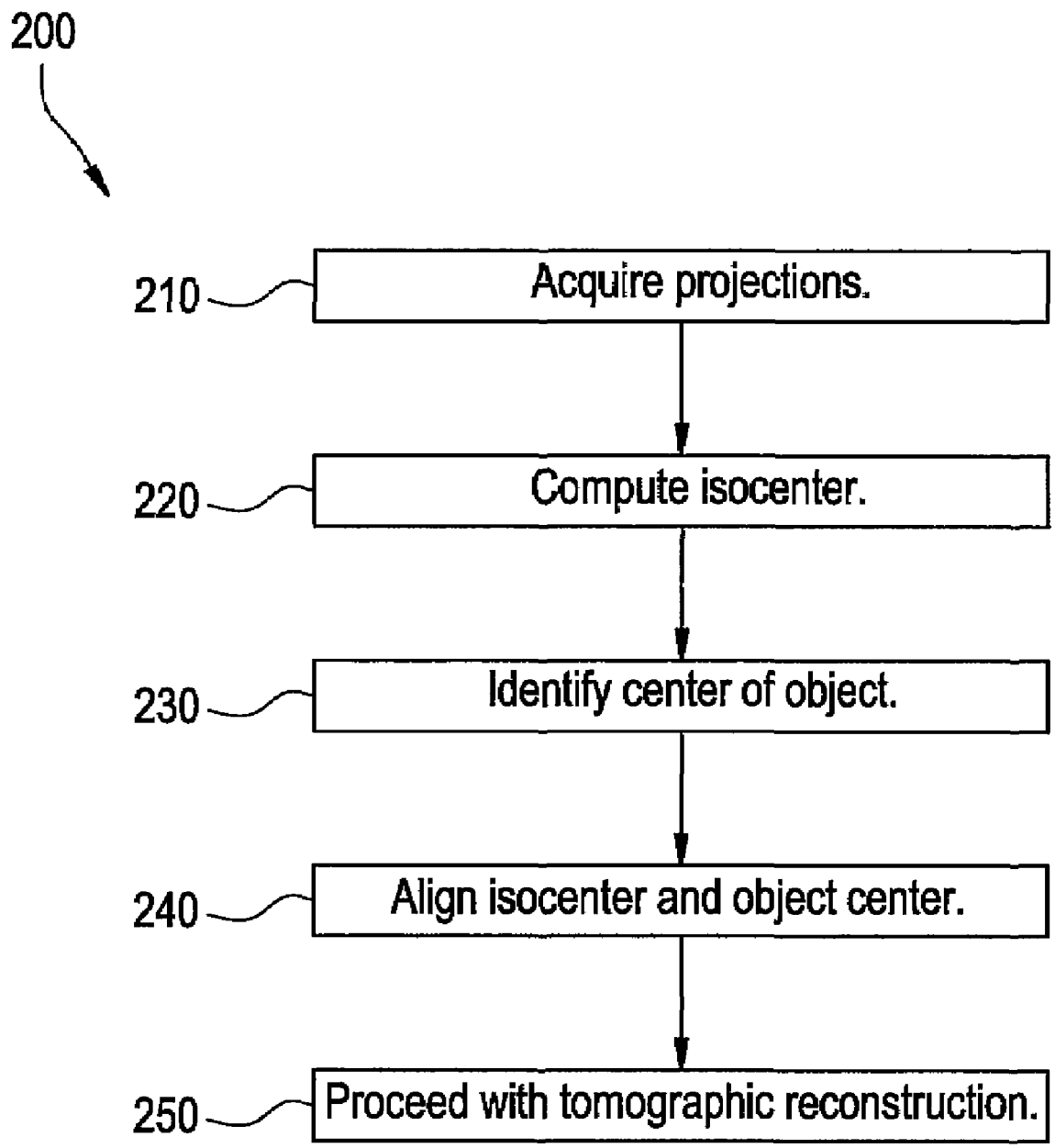
FIG. 2 illustrates a flow diagram for a method for isocenter positioning of an object in an image acquisition system used in accordance with an embodiment of the present invention.

FIG. 2 illustrates a flow diagram for a method 200 for isocenter positioning of an object in an image acquisition system used in accordance with an embodiment of the present invention. First, at step 210, projections or EM receiver 120 positions are acquired (lateral and frontal, for example). For example, frontal and lateral x-ray projections from an x-ray source to the x-ray detector 130 are obtained with the EM receiver 120 at the x-ray detector 130. Then, at step 220, an isocenter is computed with respect to a position of the EM emitter 110. For example, the isocenter is computed based on vectors and focal spots from the x-ray projections. In an embodiment, the isocenter is located approximately halfway along a segment orthogonally connecting the x-ray projections.

Figure 3:
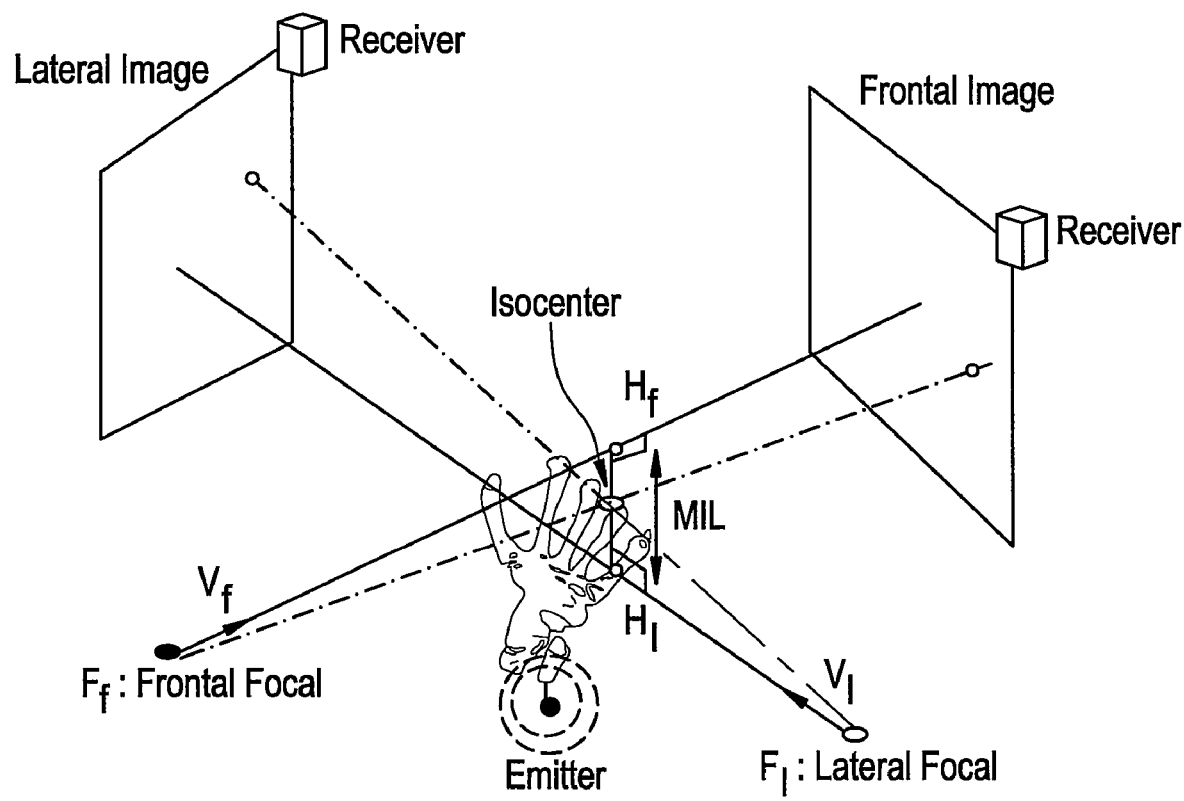
FIG. 3 illustrates frontal and lateral x-ray projections through an object to be imaged in accordance with an embodiment of the present invention.

FIG. 3 illustrates frontal and lateral x-ray projections through an object to be imaged in accordance with an embodiment of the present invention. A lateral focal point $F_l$ and a lateral projection vector $v_l$ produce a lateral image at the x-ray detector 130 with EM receiver 120. A frontal focal point $F_f$ and a lateral projection vector $v_f$ produce a frontal image at the x-ray detector 130. The focal points $F_l$ and $F_f$ and vectors $v_l$ and $V_f$ may be determined through calibration. Then, a vector n may be determined from $v_l$ and $v_f$ as follows:

$$\vec{n} = \frac{\vec{v}_f \wedge \vec{v}_l}{\|\vec{v}_f \wedge \vec{v}_l\|}. \quad (1)$$

Then, locations $H_l$ and $H_f$ along vectors $v_l$ and $v_f$, respectively, may be determined from the following equations, for example:

$$H_f = F_f + \left(\frac{(\vec{v}_l \wedge \vec{n}) \cdot \vec{F}_f \vec{F}_l}{(\vec{v}_l \wedge \vec{n}) \cdot \vec{v}_f}\right)\vec{v}_f, \text{ and} \quad (2)$$

$$H_l = F_l + \left(\frac{(\vec{v}_f \wedge \vec{n}) \cdot \vec{F}_f \vec{F}_l}{(\vec{v}_f \wedge \vec{n}) \cdot \vec{v}_l}\right)\vec{v}_l. \quad (3)$$

Using $H_l$ and $H_f$, the isocenter (I) may be calculated as $$I = \frac{1}{2}\vec{H}_f \vec{H}_l. \quad (4)$$

The isocenter is determined with respect to the EM emitter 110 on the object 140. Alternatively, if an approximate focal distance is determined, vectors $v_f$ and $v_l$ and the focal points $F_f$ and $F_l$ may be determined using position and orientation information from the EM emitter 110 without acquiring x-ray images.

Figure 4:
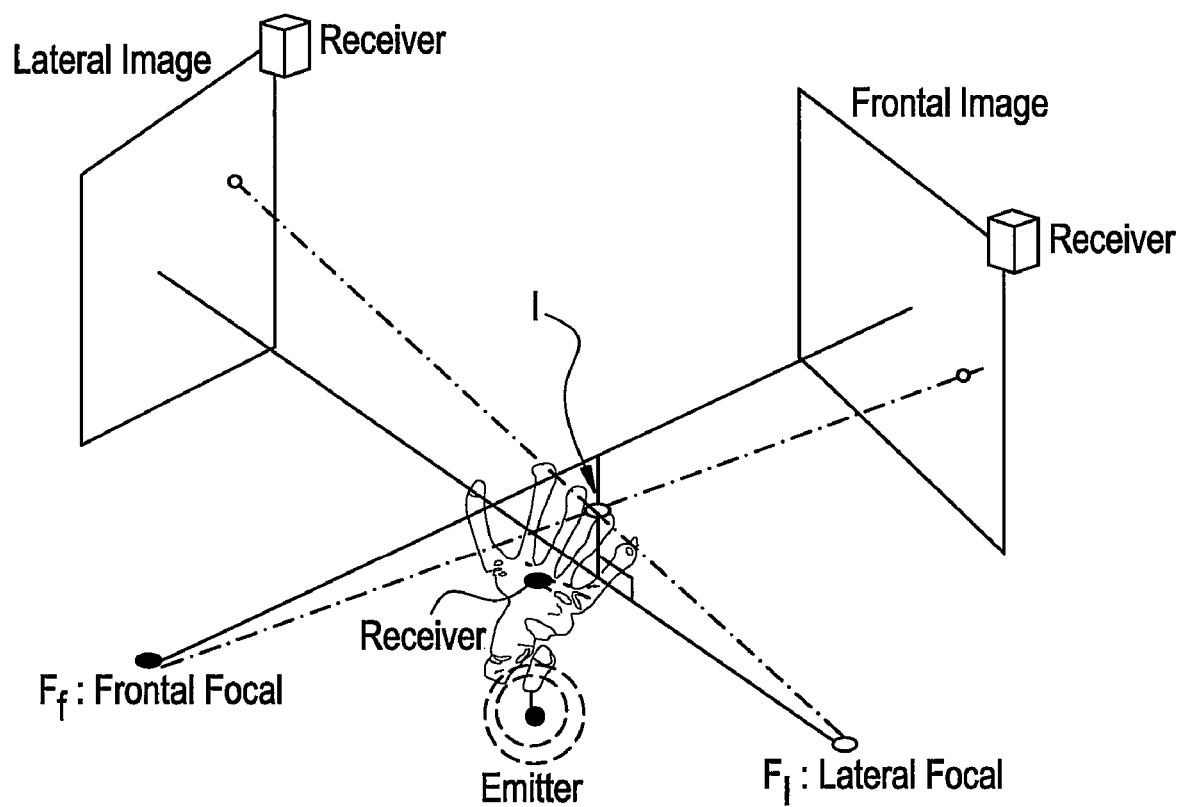
FIG. 4 depicts a tool with an electromagnetic receiver pointing to the center of an object in accordance with an embodiment of the present invention.
Figure 5:
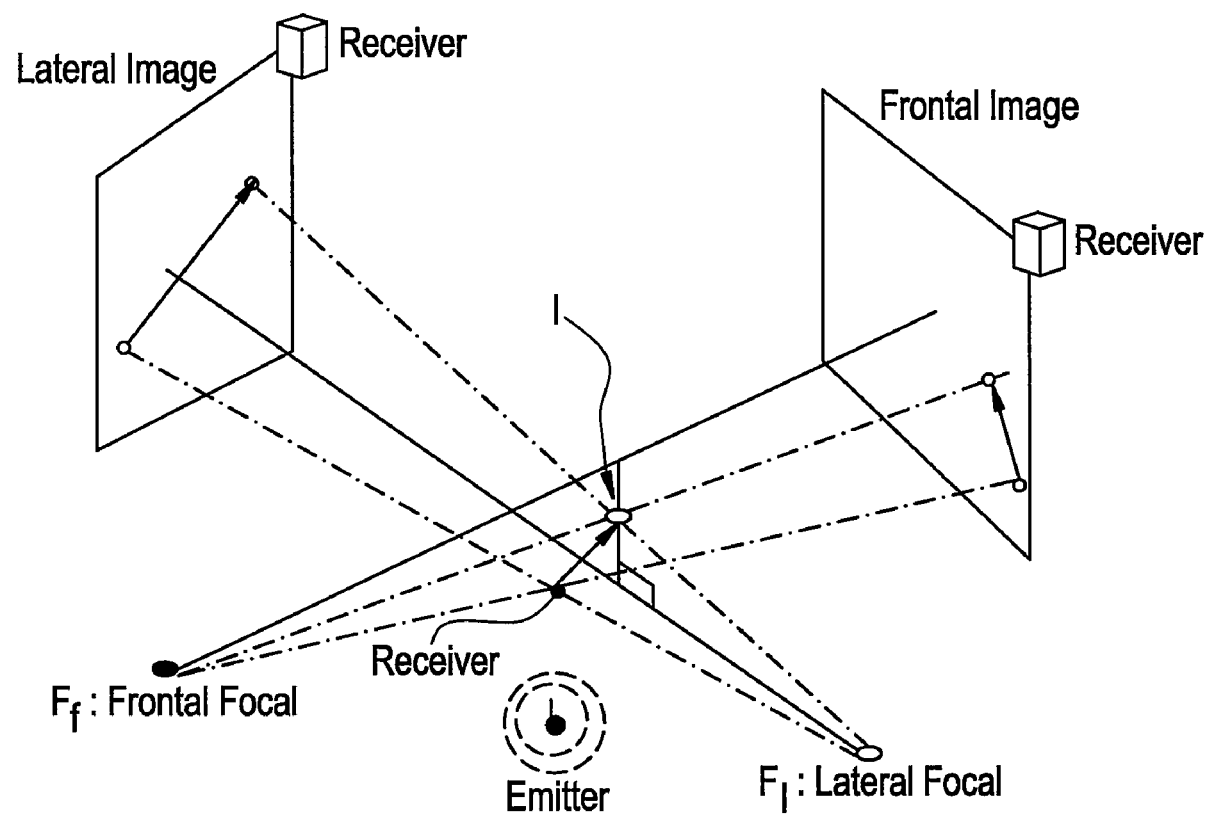
FIG. 5 illustrates aligning the isocenter and object center position in accordance with an embodiment of the present invention.

Next, at step 230, a center position of the object 140 for tomographic acquisition is identified using the tool 150 with the attached EM receiver 125. FIG. 4 depicts a tool 150 with EM receiver 125 pointing to the center of an object 140 in accordance with an embodiment of the present invention. Then, at step 240, the object 140 is positioned such that the center position identified in step 230 is aligned with respect to the isocenter. Positioning may be accomplished manually (with a manual positioning system or table, for example) and/or automatically (with a motorized table or positioning system, for example). For example, a fixed motorized table in a vascular C-arm x-ray system may move a patient until the center of an organ of interest approximately matches the isocenter of the C-arm system. FIG. 5 illustrates aligning the isocenter and object center position in accordance with an embodiment of the present invention. At step 250, tomographic reconstruction of the object 140 may proceed.

Figure 6:
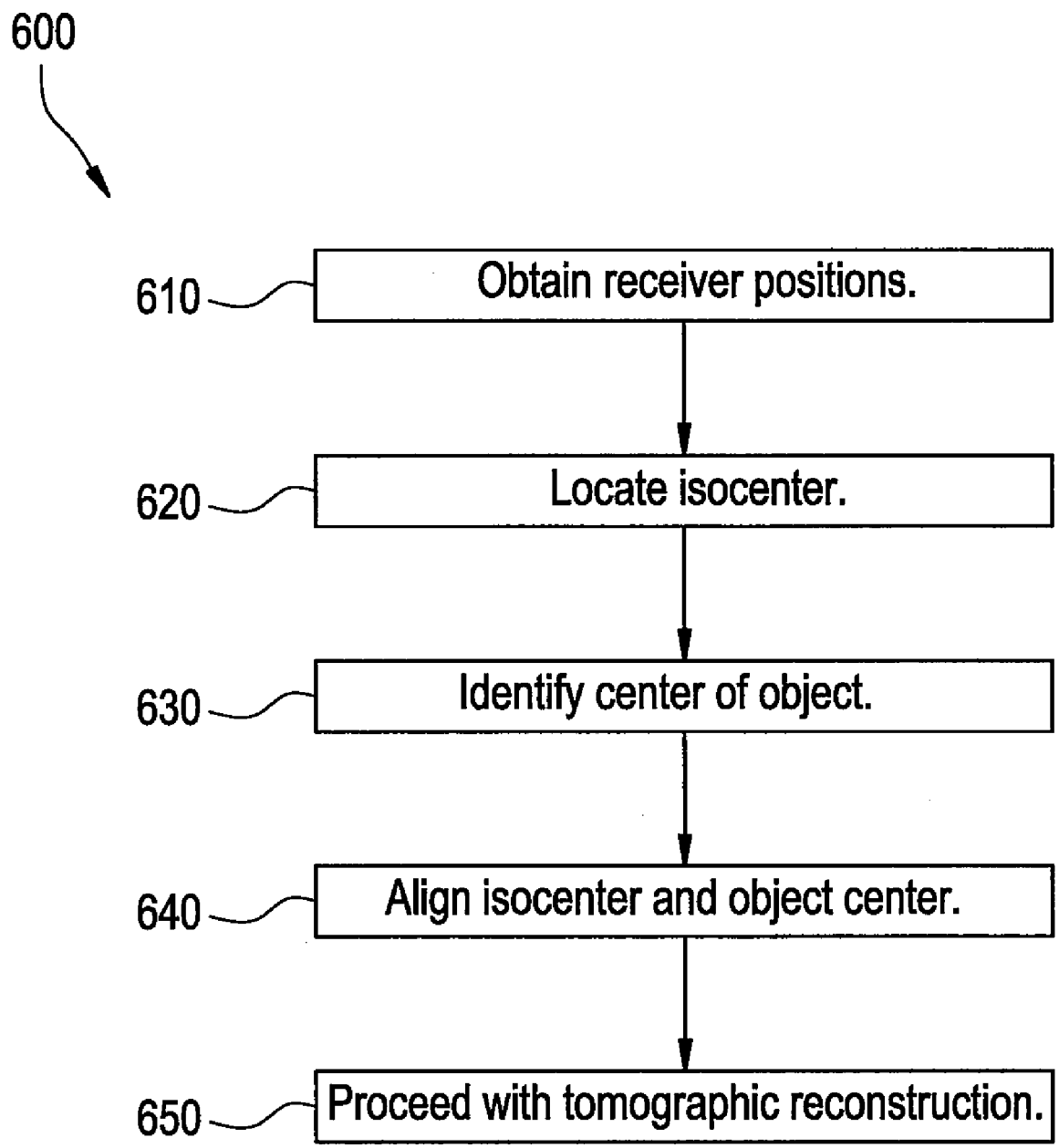
FIG. 6 illustrates a flow diagram for a method for isocenter identification and object positioning used in accordance with an embodiment of the present invention.
Figure 7:
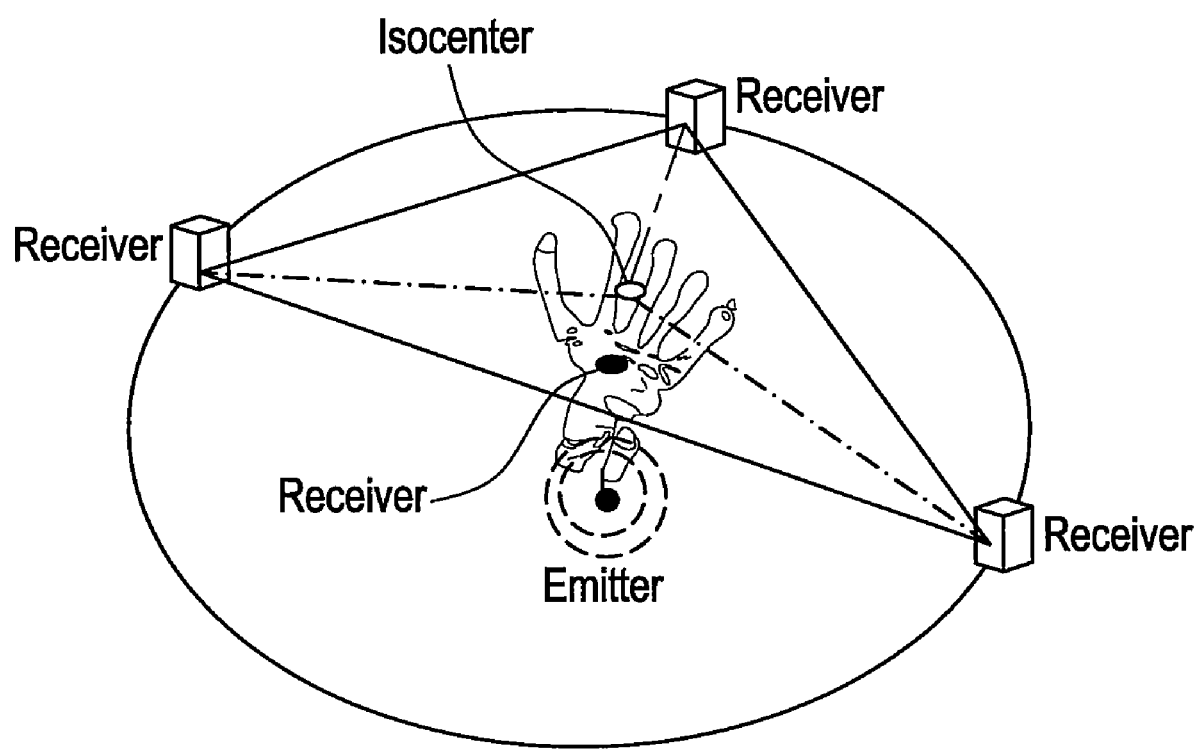
FIG. 7 illustrates isocenter position with a plurality of electromagnetic receivers in accordance with an embodiment of the present invention.

In another embodiment, the isocenter of an acquisition system may be determined without preliminary scans or projections. FIG. 6 illustrates a flow diagram for a method 600 for isocenter identification and object positioning used in accordance with an embodiment of the present invention. First, at step 610, three or more positions of the EM receiver 120 attached to the x-ray detector 130 are obtained. The EM receiver 120 allows the center of the detector 130 to be recorded during a tomographic acquisition without x-ray projections, for example. The three positions of the detector 130 form vertices of a triangle.

Then, at step 620, the isocenter is located based on the triangle. In an embodiment, the isocenter corresponds to the center of the triangle. The isocenter (I) may be determined in the plane of the triangle by solving the following system of equations:

$$\begin{vmatrix} x^2+y^2 & x & y & 1 \\ x_1^2+y_1^2 & x_1 & y_1 & 1 \\ x_2^2+y_2^2 & x_2 & y_2 & 1 \\ x_3^2+y_3^2 & x_3 & y_3 & 1 \end{vmatrix} = 0, \quad (5)$$

where $$\begin{pmatrix} x_1 \\ y_1 \end{pmatrix}, \begin{pmatrix} x_2 \\ y_2 \end{pmatrix}, \text{ and } \begin{pmatrix} x_3 \\ y_3 \end{pmatrix}$$

are coordinates of the three detector 130 positions expressed in the plane of the triangle.

If more than three detector 130 positions are acquired, the isocenter corresponds to the center of a mean circle or ellipse projected in a mean plane of the acquired detector 130 positions. First, the mean plane corresponding to the acquired positions is determined by minimizing the following criteria:

$$\sum_{i=0}^{n} |ax_i + by_i + cz_i + d|, \quad (6)$$

where $$\begin{pmatrix} x_i \\ y_i \\ z_i \end{pmatrix}$$

represent the acquired three-dimensional positions of the center of the detector 130. Then, the mean circle is computed using projected positions $$\begin{pmatrix} x_i \\ y_i \end{pmatrix}$$

of the acquired positions in the mean plane. The mean circle is determined by minimizing the following criteria:

$$\sum_{i=0}^{n} |(x_i - c_x)^2 + (y_i - c_y)^2 - R^2|. \quad (7)$$

The mean ellipse is determined using the following equation:

$$\sum_{i=0}^{n} \left| \frac{(x_i - c_x)^2}{a^2} + \frac{(y_i - c_y)^2}{b^2} - 1 \right|. \quad (8)$$

Alternatively, the isocenter may be determined based on an electromagnetic orientation of the acquired detector 130 positions and an approximate value of a source-to-image distance. The source-to-image distance may be determined through calibration, for example. Then, the positions may be back-projected to determine the isocenter.

Next, at step 630, a center position of the object 140 for tomographic acquisition is identified using the tool 150 with the attached EM receiver 125. Then, at step 640, the object 140 is positioned such that the center position identified in step 630 is aligned with respect to the isocenter. Positioning may be accomplished manually (with a manual positioning system or table, for example) and/or automatically (with a motorized table or positioning system, for example). For example, a fixed motorized table in a vascular C-arm x-ray system may move a patient until the center of an organ of interest is aligned with the isocenter of the C-arm system. At step 650, tomographic reconstruction of the object 140 may proceed.

In an embodiment, a "good" working position may be defined mathematically by expressing some properties of the position, for example. Position properties may differ depending upon the organ or object being reconstructed. Properties may also vary depending upon the tool used to locate the object center prior to alignment. Certain embodiments provide a variety of methods to determine a good position for tomographic reconstruction using EM navigation devices, such as an EM emitter and an EM receiver. A good working position for a three-dimension tomographic acquisition may be easily and quickly identified using receiver and transmitter devices connected to a detector and an object, such as a patient. Efficient position determination saves radiation dosage during centering of the object.

Thus, certain embodiments of the present invention position an object with respect to the isocenter of an acquisition system to facilitate tomographic image reconstruction. Certain embodiments provide for semi-automatic positioning of an organ or other object for three-dimensional reconstruction using EM navigation devices. Certain embodiments provide for positioning for optimal tomographic acquisition without image exposures or with a minimum number of exposures. EM navigation devices may be used to determine an optimal position for image reconstruction.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for positioning an object at an isocenter of an imaging system, said method comprising:
   acquiring two x-ray projections in an imaging system;
   emitting a magnetic field using an electromagnetic emitter;

detecting the magnetic field using an electromagnetic receiver;

determining an isocenter for the imaging system using the two x-ray projections and information from the electromagnetic receiver;

locating a center position of an object to be imaged using information from the electromagnetic receiver, wherein at least one of the electromagnetic emitter and the electromagnetic receiver is located on the object to be imaged; and positioning the center position of the object with respect to the isocenter.

2. The method of claim 1, wherein said determining step further comprises determining the isocenter using a segment intersecting the x-ray projections.

3. The method of claim 1, wherein said aligning step further comprises at least one of manually and automatically moving the object to position the center position with respect to the isocenter.

4. The method of claim 1, wherein the electromagnetic emitter is located on the object to be imaged and the electromagnetic receiver is located on an x-ray detector.

5. The method of claim 1, wherein the electromagnetic emitter is located on the object to be imaged and the electromagnetic receiver is located on a tool configured to point to the center of the object to be imaged.

6. The method of claim 1, wherein the electromagnetic receiver is located on the object to be imaged and the electromagnetic emitter is located on an x-ray detector.

7. The method of claim 1, wherein the electromagnetic receiver is located on the object to be imaged and the electromagnetic emitter is located on a tool configured to point to the center of the object to be imaged.

8. A method for centering an object in an imaging system, said method comprising:

acquiring at least three position measurements for an electromagnetic receiver in an imaging system, wherein the electromagnetic receiver is configured to detect a magnetic field and the electromagnetic receiver is located on a detector of the imaging system; and computing an isocenter with respect to an electromagnetic emitter using the at least three position measurements, wherein the electromagnetic emitter is configured to emit a magnetic field.

9. The method of claim 8, further comprising:

indicating a center position of the object; and moving the object such that the isocenter and the center position are aligned.

10. The method of claim 9, wherein said moving step further comprises at least one of manually and automatically moving the object such that the isocenter and the center position match.

11. The method of claim 8, wherein said computing step further comprises computing the isocenter based on a center of the at least three position measurements.

12. The method of claim 8, wherein the electromagnetic emitter is located on the object to be imaged.

13. A method for determining a working position for tomographic reconstruction, said method comprising:

calculating an approximate focal distance in an imaging system;

determining position and orientation information for an electromagnetic receiver with respect to an electromagnetic emitter in the imaging system, wherein the electromagnetic emitter is configured to emit a magnetic field and the electromagnetic receiver is configured to detect the magnetic field, and wherein at least one of the electromagnetic emitter and the electromagnetic receiver is located on an object to be imaged; and identifying an isocenter for the imaging system using the position and orientation information and approximate focal distance.

14. The method of claim 13, wherein said identifying step further comprises back-projecting the position information to identify the isocenter.

15. The method of claim 13, further comprising:

indicating a center position of an object around which a tomographic acquisition may be performed; and moving the object such that the isocenter and the center position are aligned.

16. The method of claim 15, wherein said moving step further comprises at least one of automatically and manually moving the object such that the isocenter and the center position are aligned.

17. The method of claim 13, wherein the electromagnetic emitter is located on the object to be imaged and the electromagnetic receiver is located on a detector of the imaging system.

18. The method of claim 13, wherein the electromagnetic emitter is located on the object to be imaged and the electromagnetic receiver is located on a tool configured to point to the center of the object to be imaged.

19. The method of claim 13, wherein the electromagnetic receiver is located on the object to be imaged and the electromagnetic emitter is located on a detector of the imaging system.

20. The method of claim 13, wherein the electromagnetic receiver is located on the object to be imaged and the electromagnetic emitter is located on a tool configured to point to the center of the object to be imaged.

* * * * *